United States Patent [19]

Lares

[11] Patent Number: 4,534,734
[45] Date of Patent: Aug. 13, 1985

[54] SWIVEL DENTAL HANDPIECE
[75] Inventor: Joseph P. Lares, Redwood City, Calif.
[73] Assignee: Lares Research, San Carlos, Calif.
[21] Appl. No.: 502,492
[22] Filed: Jun. 9, 1983
[51] Int. Cl.³ .............................................. A61C 1/08
[52] U.S. Cl. ..................................... 433/126; 433/82
[58] Field of Search ..................... 433/126, 82, 84, 80
[56] References Cited

U.S. PATENT DOCUMENTS

| | | | |
|---|---|---|---|
| 3,936,940 | 2/1976 | Loge | 433/126 |
| 4,175,323 | 11/1979 | Eibofner et al. | 433/126 |
| 4,260,382 | 4/1981 | Thomson | 433/29 |
| 4,353,697 | 10/1982 | Nakanishi | 433/126 |
| 4,354,839 | 10/1982 | Schuss | 433/126 |
| 4,403,956 | 9/1983 | Nakanishi | 433/126 |
| 4,403,958 | 9/1983 | Lohn | 433/126 |
| 4,403,959 | 9/1983 | Hatakeyama | 433/126 |

Primary Examiner—John J. Wilson
Attorney, Agent, or Firm—Lothrop & West

[57] ABSTRACT

An elongated dental handpiece with an air turbine at one end and a supply hose at the other end has two disconnectable casings coupled to swivel about its longitudinal axis. The various supplies for the turbine, including turbine drive air, chip air, water and light, extend through the swivel. Exhaust air from the turbine is carried through all of one casing and is released to the atmosphere in the area where the casings can be disconnected.

5 Claims, 10 Drawing Figures

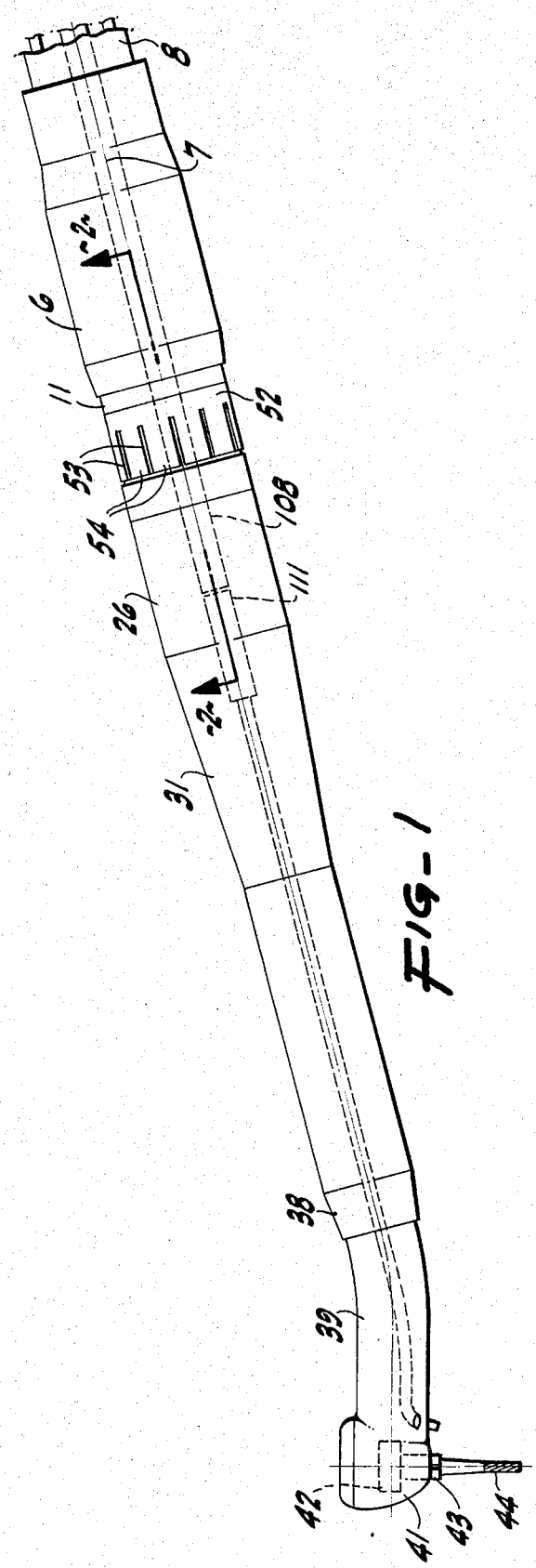
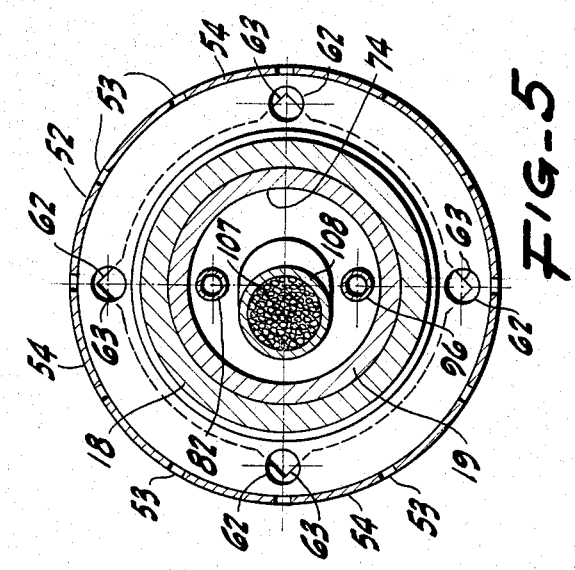
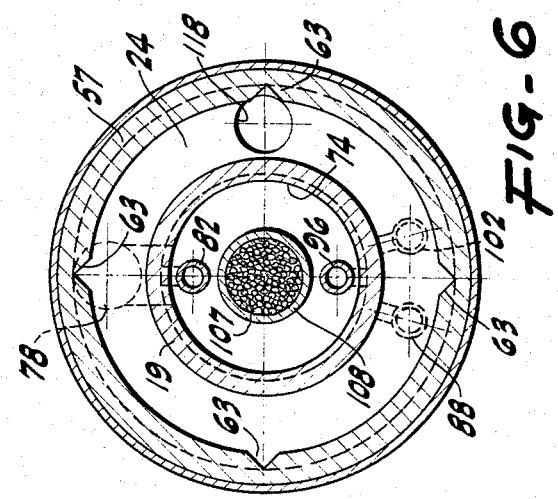
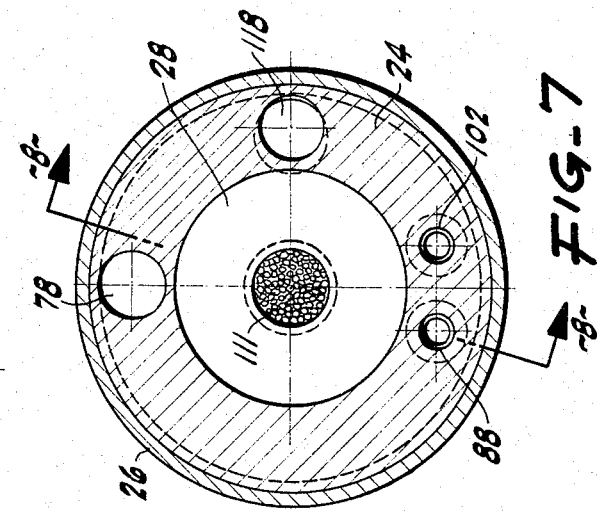

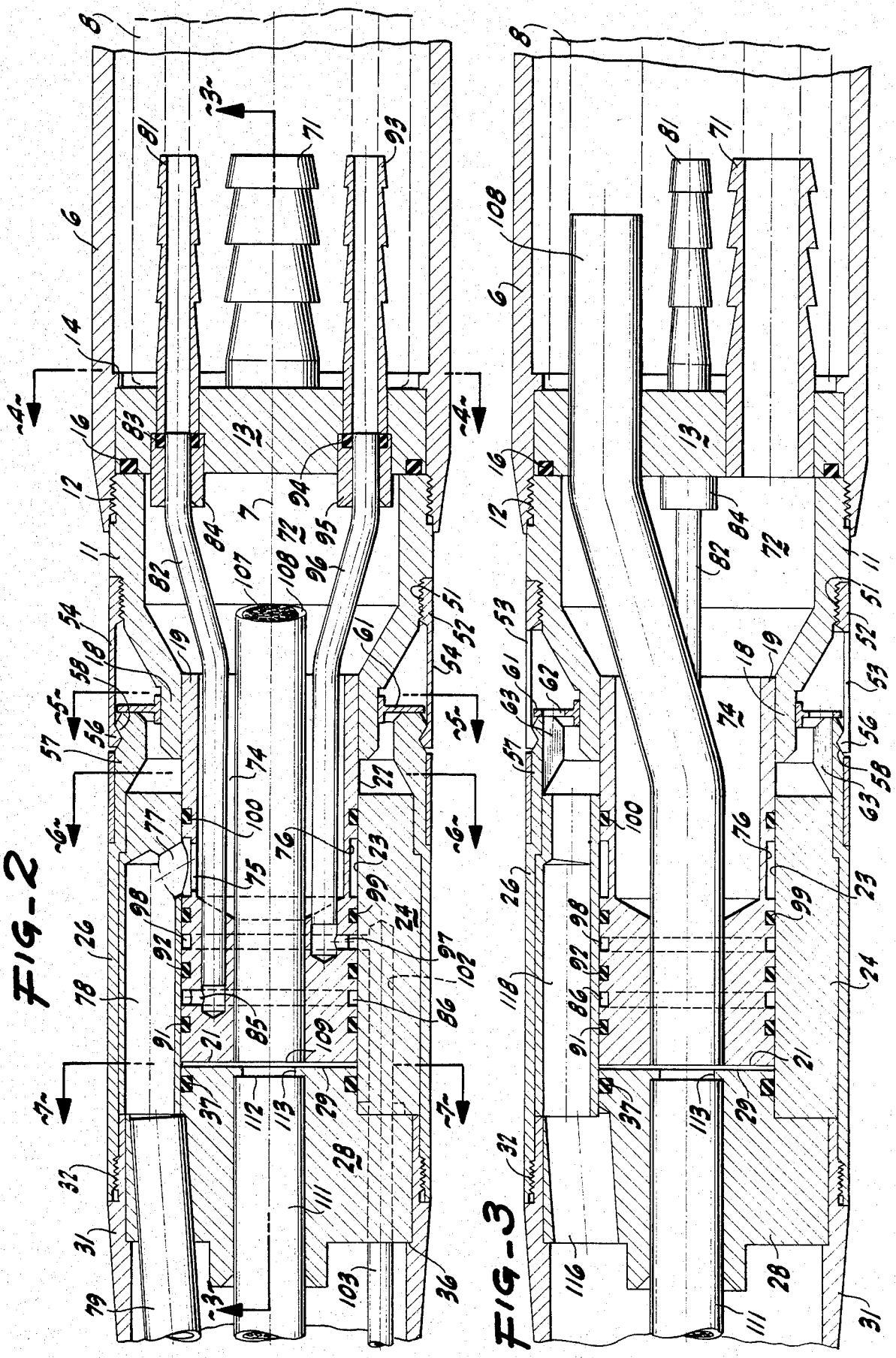

SWIVEL DENTAL HANDPIECE

CROSS-REFERENCES TO RELATED APPLICATIONS

Reference is made to co-pending application Ser. No. 248,866, filed Mar. 30, 1981 and entitled "Dental Handpiece", now U.S. Pat. No. 4,431,412, issued 02/14/84.

BRIEF SUMMARY OF THE INVENTION

A dental handpiece extending along an axis has a pair of casings arranged separably in line and concentrically on the axis to swivel with respect to each other. The handpiece at one end carries a turbine housing within which an air turbine drives a chuck for a dental drill. Feeding into the handpiece is a hose containing a number of supply lines for driving air, chip air, water and light. Supplies from the various lines extend through the swivel mechanism to the turbine end. Exhaust air from the turbine is carried through at least one of the swivel casings and is exhausted quietly to the atmosphere in or near the zone in which the handpiece is held.

PRIOR ART

No prior art is known to applicant that is in detail concerned with a two-casing, swivel, air turbine handpiece having various air and water supply lines extending therethrough as disclosed herein nor having a mechanism for releasing turbine exhaust air to the atmosphere through slots between multiple fingers releasably holding the casings together.

BRIEF DESCRIPTION OF THE SEVERAL VIEWS OF THE DRAWINGS

FIG. 1 is a side elevation of a complete dental handpiece pursuant to the invention with the supply hose connected thereto and broken away.

FIG. 2 is a view to an enlarged scale, the view being in cross-section, the plane of which is indicated by the line 2—2 of FIG. 1.

FIG. 3 is a cross-section comparable to FIG. 2 but with the plane of cross-section taken at a right angle to that of FIG. 2.

FIG. 5 is a cross-section, the plane of which is indicated by the line 5—5 of FIG. 2.

FIG. 6 is a cross-section, the plane of which is indicated by the line 6—6 of FIG. 2.

FIG. 7 is a cross-section, the plane of which is indicated by the line 7—7 of FIG. 2.

DETAILED DESCRIPTION

Figure 4:
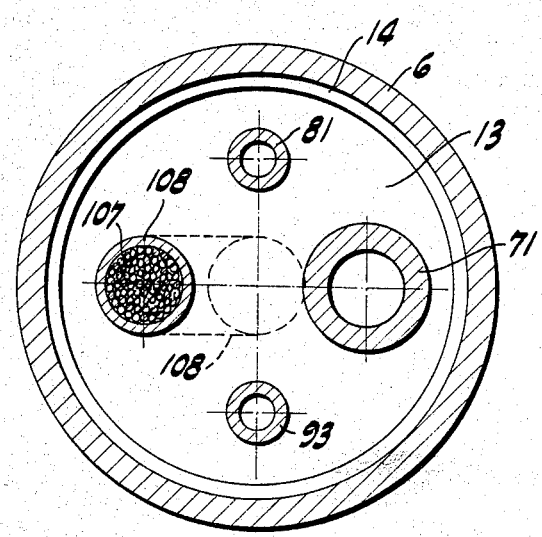
FIG. 4 is a transverse cross-section, the plane of which is indicated by the line 4—4 of FIG. 2.

The swivelling dental handpiece pursuant to the invention is preferably inclusive of a first, hollow outer casing 6, preferably including one or more separate parts, is circular in transverse section and is symmetrical about a longitudinal axis 7. At one end the hollow casing receives and is detachably connected to a hose 8 within which there are several tubes or conductors for supply items joined to individual terminals within the sleeve (see FIG. 2).

Included with the first hollow casing 6 is a bell housing 11 also symmetrical about the axis 7 and having a threaded connector 12 with the casing 6 and serving, when assembled, to clamp in place a perforated barrier plate 13 resting against a shoulder 14 in the casing 6. A sealing ring 16 affords an appropriate seal against leakage.

The bell housing 11 is extended along the axis and is reduced in diameter to merge with a collar 18 engaged with a hollow hub 19 likewise extending along the axis and terminating in a transverse end face 21. The collar 18 and hub 19 are made either in one piece or in two pieces, but in either event they always act unitarily.

The hollow hub 19 is particularly provided with an exterior, circular, cylindrical journal surface 22 concentric with the axis and in rotatable engagement with a comparable surface 23 on the interior of a sleeve 24. This sleeve lies just inside of a second hollow casing 26, concentric with the axis and in effect extending the first hollow casing 6. The sleeve 24 is in engagement with a supporting block 28 abutting one end face of the sleeve 24. The block 28 also has a transverse end face 29 normal to the axis and parallel to and slightly spaced from the transverse end face 21 of the rotary hub 19. The block 28 at its periphery is held in position by an extended portion 31 of the second hollow casing having a threaded engagement 32 with the portion 26. The supporting block 28 is forced to abut the end of the sleeve 24 and to abut a shoulder 36 in the extended portion 31. A packing or sealing ring 37 seals the joint between the sleeve 24 and the supporting block 28.

The extended portion 31 of the secondary casing 26 extends to a reduced portion 38 leading to a straight casing portion 39 merging with a turbine housing 41. Within the housing in suitable bearings there is mounted a turbine runner 42 having a chuck 43 for reception of a dental burr 44, for example.

In order releasably to interconnect the first hollow casing 6 and the second hollow casing 26, there is provided on the bell housing 11 a threaded section 51 within a ring 52 having a number of axially extending, open slots 53 (FIG. 1) affording intervening flexible fingers 54. At the ends of the fingers there are enlargements 56 designed flexibly to interengage with and to cam over, when deflected, a subjacent ring 57 extended from the second exterior housing 26 and having a peripheral groove 58 for receiving the enlargements 56. The interengagement of the enlargements 56 and the groove 58 keeps the surfaces 21 and 29 slightly apart. Also mounted on the bell housing is a ring 61, T-shaped in cross-section and having a number of openings 62 therethrough. These openings can be omitted. Air then goes around the periphery of the ring 61. There are axial slots 63 in the ring 57 near the openings 62 for wrench engagement as an assistance in screwing the casing 26 and portion 31 together or apart.

With this arrangement, although the springiness of the fingers 54 is normally sufficient to preclude axial separation of the two casings of the handpiece, there is no restriction by these parts against complete relative rotation of the two handpiece casings. Yet, if a strong axial separating force is imposed on the two handpiece casings 6 and 26, the spring fingers 54 yield outwardly so that the enlarged ends 56 cam over the ring 57 to permit axial separation. Even though the fingers 54 are springy, they cannot accidentally be deflected inwardly because of support by the ring 61. There is thus provided a swivelling two-part handpiece. Normally the relatively rotatable casings are held together, but they can be separated by a substantial axial force and reassembled by a similar, opposite axial force. The casings 6 and 26 are readily disconnected from each other for internal inspection and oiling and so that each may be replaced by a different form of handpiece casing especially for use with different operating tools.

An air supply line in the hose 8 is joined to a drive air fitting 71 pressed into and seated in the barrier plate 13 and opening into the interior volume 72 of the bell housing 11. That drive air can flow into the interior 74 of the hollow hub 19 and thence through a radial aperture 75, or several such apertures, into a circular groove 76 in the hub wall. The drive air path is then from that groove through a joining opening 77 merging with a conducting bore 78 in the sleeve 24. A drive air tube 79 positioned in the supporting block 28 takes the drive air from the bore 78 to the turbine housing 41 so the drive air can discharge onto the turbine runner 42 in the usual way.

Figure 8:
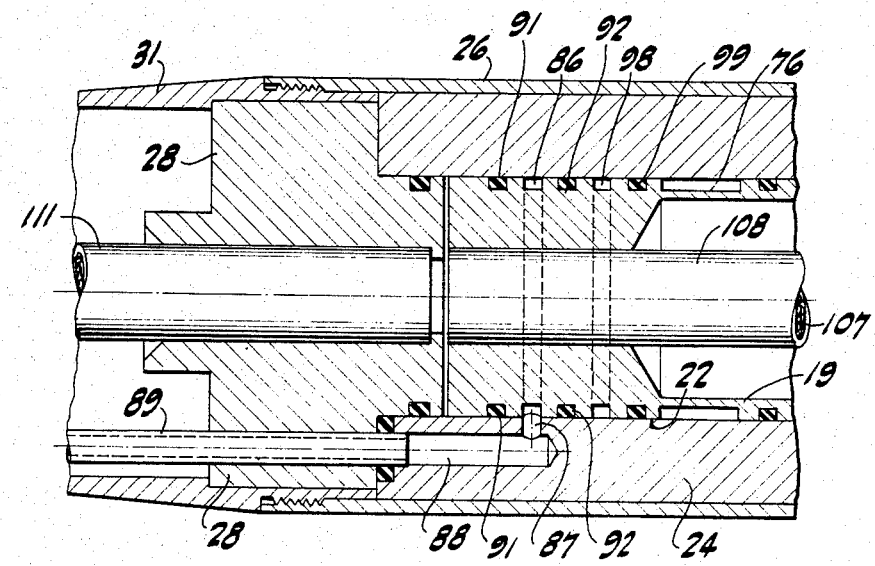
FIG. 8 is a detail in cross-section with portions broken away, the plane of section being indicated by the line 8—8 of FIG. 7.

Also contained in the hose 8 is a supply of chip air with an appropriate tube joined to a chip air fitting 81, also seated in the barrier plate and connected to a tube 82. An appropriate seal 83 held in place by a collar 84 precludes leakage. The tube 82 travels through the hollow interior of the hub 19 and opens into a cross bore 85 merging with a surrounding groove 86 in the hub. In communication with the groove 86 is a radial passage 87 (FIG. 8) leading into a bore 88 in the sleeve 24. A tube 89 fits into the bore 88 and extends to and emerges from the second hollow casing 26 near the turbine housing 41. To preclude air leakage there are sealing rings 91 and 92 either side of the groove 86.

Figure 9:
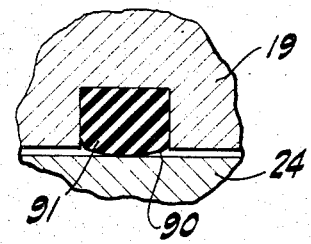
FIG. 9 is a detail in cross-section like FIG. 8, but showing to an enlarged scale a sealing ring and its immediately adjacent structure.

These sealing rings can be the customary O-rings, but preferably have a special shape in cross-section as shown in FIG. 9. The rings preferably are not circular in cross-section but are more nearly D-shaped. They fill their respective grooves in the portions away from the rubbing surface, but adjacent the rubbing surface they have a flattened arc or approximately hemi-elliptic, shaped face 90. This contour helps to prevent rolling or twisting of the ring as the adjacent parts are moved axially. The rings thus stay in position for good sealing despite both rotary and endwise motion.

In a similar fashion, from the hose 8 a water tube engages with a fitting 93 seated in the barrier plate 13 and protected against leakage by a sealing ring 94. A thimble 95 pressed into the barrier plate carries a water tube 96 through the hollow interior of the hub 19 and leading through a cross bore 97 into a peripheral groove 98. This is protected on opposite sides by the sealing ring 92 and another, comparable ring 99. The groove 76 is similarly sealed on opposite sides by rings 99 and 100. The groove 98 opens into a longitudinal water passage 102 in the sleeve 24 and continues through a corresponding duct 103 to a discharge location in the second hollow casing 26 near the turbine housing 41.

Since it is preferred to have illumination near the site of operation of the burr, and since light can be made available in the hose 8 through optical fibers therein, a bundle 107 of such fibers and their enclosing sheath 108 are brought in an axial direction but off center through the first casing 6. They pass through the barrier plate 13 as a support. The optical bundle 107 is then deflected from its off-axis position into a position concentric with the axis and extends along the axis through the hub 19 and terminates with a transverse end face 109 coplanar with the transverse end face 21.

On the axis near the end of the bundle 107 is a second fiber optic bundle 111, preferably sheathed, and having a planar end face 112 parallel to the end face 109 but slightly spaced therefrom. The bundle 112 is positioned endwise by an internal flange 113 extending from the supporting block 28. The fiber optic bundle 111 extends axially for a selected distance within the second casing 26 and then protrudes therefrom in the vicinity of the burr 44. Preferably, the bundle 111 is divided into two portions somewhat in advance of the burr and projects on opposite sides of the burr to afford two beams of light projected to either side of the dental tool.

The driving air for the turbine, after use, and now exhaust air, in a minor part is discharged through the turbine housing bearings to the immediate surroundings. There is afforded a controlled exhaust flow of the remaining, major amount of the turbine discharge air. Exhaust air is released from the turbine into the interior of the second hollow casing 26 and flows into and through a passage 116 in the supporting block 28. The exhaust air then continues to flow through a passage 118 in the sleeve 24 into the interior of the second casing 26. Finally the exhaust flow is through the axial slots 63 at the end of the second casing to discharge through the openings 62 in the support ring and then through the slots 53 to the atmosphere. Thus the exhaust air from the turbine is brought to the atmosphere at a convenient point, and in passing through the relatively large area, afforded by all of the slots together, effects a relatively quiet, nondisturbing exit.

Figure 10:
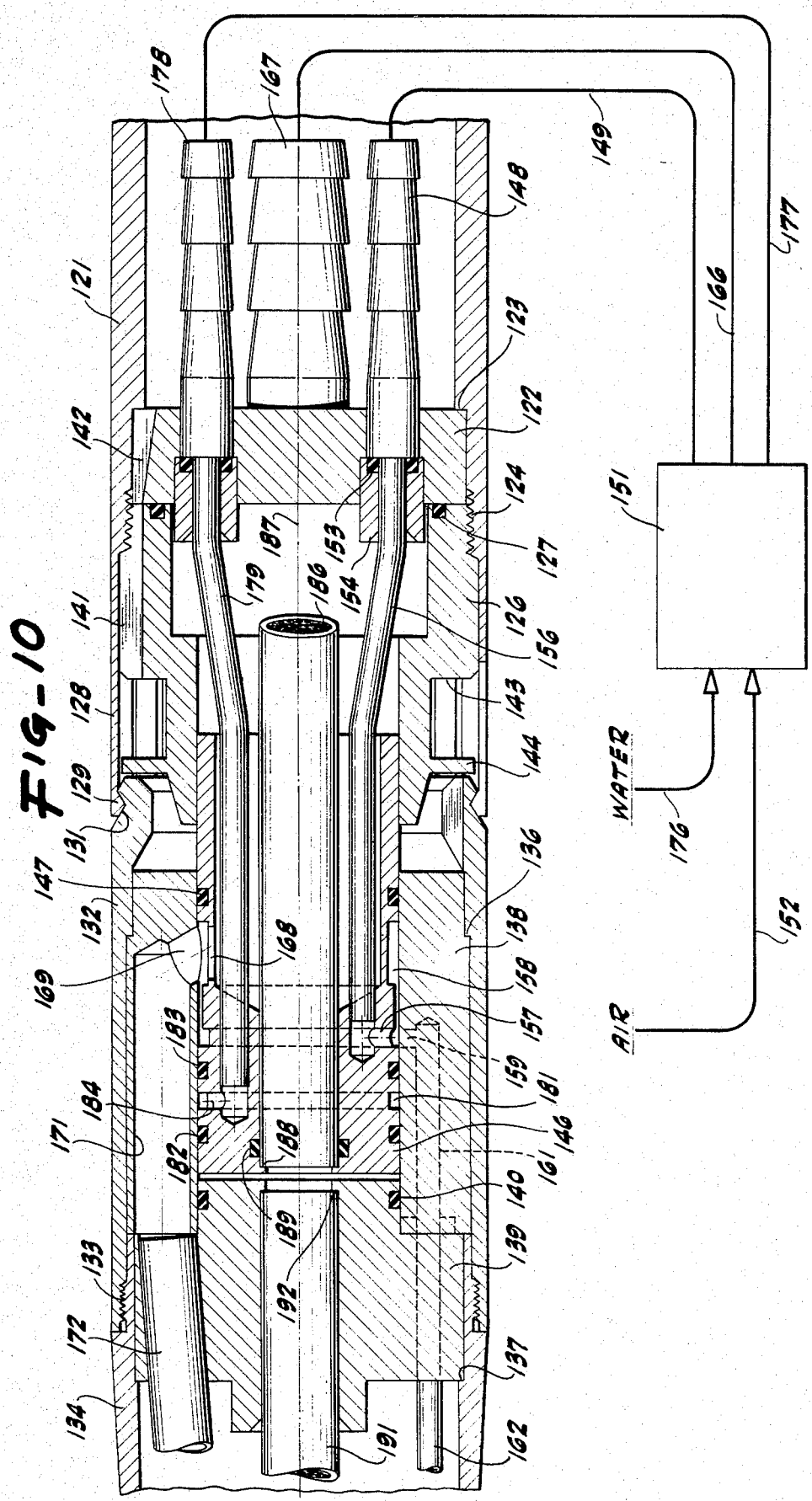
FIG. 10 is a view in cross-section, like FIG. 2, but showing a modified form of construction with fewer but more integrated parts.

In the arrangement shown in FIG. 10, most of the structure is as before, but there are some changes, primarily for simplification. The first hollow casing 121 overlies a barrier plate 122 which abuts against a shoulder 123. The first casing 121 has threads 124 engaging one end of a bell housing 126, there being a sealing ring 127 against the abutting faces of these parts. The first casing 121 is also extended past the threads 124 to form a plurality of integral, springy fingers 128 having enlarged ends 129 receivable in a groove 131 in an aligned second hollow casing 132. Threads 133 join the casing 132 with an end portion 134. Shoulders 136 and 137 on the parts 132 and 134 engage the ends of a sleeve 138 and of a supporting block 139 and urge those parts together. A seal ring 140 prevents leakage therebetween. The bell housing 126 and the barrier plate 122 both have edge passages 141 and 142 allowing free communication between the hollow interior of the casing 121 and a groove 143 on the bell housing 126, the groove 143 itself communicating through ample clearance space around a flange 144 on the bell housing 126 and the interior of the casing 132. Preferably pressed into the bell housing 126 and disposed coaxially thereof is a hollow hub 146 having, if desired, a sealing ring 147, preferably a "D" ring, between the hub 146 and the sleeve 138.

Within the casing 121, preferably with adequate clearance for connections and bending, is a chip air fitting 148 for the reception of a chip air hose 149 from a control 151 fed from a suitable compressed air line 152. The fitting 148 is seated in the barrier plate 122 and has a leakage seal formed by an O-ring 153 and a retainer 154. A chip air duct 156 extends from the fitting 148 to a termination in the hollow hub 146, being lodged in a bore therein having a passage 157 open to an exterior groove 158. Opening into the groove 158 is a radial bore 159 communicating with aligned ducts 161 and 162 extending to the vicinity of the turbine housing 41.

A main driving air conduit 166 extends from the source 152 and through the controller 151 to a main fitting 167 anchored in the barrier plate 122 and open to the hollow interior of the bell housing 126 and so also to the hollow interior of the hollow hub 146. There is a port 168 or several such ports open between the inside of the hollow hub and the peripheral groove 158 around the hub 146. From the groove 158 flow is had through a transition bore 169 into a longitudinal bore 171 merging with a main air duct 172 seated in the supporting block 139 and leading to the housing 41 to supply the turbine.

It will be noted that there is an air interconnection by the groove 158 between the main air or driving air supply and the chip air supply. Thus, when there is a fully supply of driving air to the turbine, some of that air can flow through the chip air conduits. The relationship and proportions of the parts are usually made such that there is only a small diversion of turbine air so that the turbine operation does not materially suffer and so that this small diversion is helpful as chip air. Also, when chip air is supplied, even though there is no main supply of turbine air, there is some diversion of chip air to the turbine. Here again, there is usually not enough diversion to drive the turbine substantially, and the remaining chip air is adequate.

There is also a water supply, as customary. Water from a suitable pressure source 176 goes through the controller 151 and and travels through a hose 177 to a fitting 178 mounted in and sealed with respect to the barrier plate 122. A water tube 179 is fitted into the hollow hub 146 and feeds into a groove 181 thereon isolated between seal rings 182 and 183. A radial bore 184 connects the continued end of the tube 179 with the groove 181, conduct of the water from the groove 181 to the vicinity of the turbine housing being substantially as previously shown and described.

Also extending through the swivel handpiece are means for conducting light. From a suitable source, not shown, a light cable 186 extends along the central axis 187 and into the hollow hub 146 and ends with a square face against a shoulder 188 therein adjacent a seal ring 189. A continuing cable 191 also has a square face directly adjacent to but spaced from the cable 186 and is lodged against a flange 192 in the supporting block 139. The cable 191 extends to the vicinity of the casing 41, where it emerges in one or more areas.

Both forms of the handpiece disclosed herein afford an easy swivelling motion, an easy disconnection of the main parts of the casing, and adequate and controlled supplies of light, water, driving air and chip air.

I claim:

1. A swivel dental handpiece comprising a first hollow casing and a second hollow casing interengaged for relative rotation about an axis and for relative movement along said axis, means including a plurality of flexible fingers for releasably holding said first and said second casings against said relative movement along said axis, said fingers having spaces between them, an air turbine in said second hollow casing, means for supplying air to said turbine, and means for exhausting air from said turbine through said second hollow casing and between said fingers directly to the atmosphere.

2. A swivel dental handpiece as in claim 1 in which the interior of said second hollow casing is substantially closed to the atmosphere and communicates therewith substantially entirely through said spaces.

3. A swivel dental handpiece comprising a first hollow casing and a second hollow casing interengaged for relative rotation about an axis and for relative movement along said axis, means defining a ring around one end of said second hollow casing, means including a plurality of circumferentially spaced flexible fingers extending axially from one end of said first housing and at their ends adapted to engage said ring, an air turbine mounted in said second hollow casing, means for supplying said turbine with driving air, and means for discharging exhaust air from said turbine directly to the atmosphere adjacent said ring and between said fingers.

4. A swivel dental handpiece as in claim 3 in which said ends of said fingers are flexible toward and away from said axis, and means on said first hollow casing limiting flexing of said fingers toward said axis.

5. A swivel dental handpiece comprising a first hollow casing concentric with an axis, a barrier plate having perforations therethrough and disposed across an end of said first hollow casing, means for sealing said barrier plate in said first hollow casing, a bell housing included in said first hollow casing and abutting said barrier plate, a hollow hub included in said first hollow casing and engaging said bell housing and having an external bearing surface concentric with said axis and having a transverse first end face, a second hollow casing concentric with said axis, a sleeve in said second hollow casing and journalled upon said bearing surface, a supporting block disposed in said second hollow casing adjacent said sleeve and concentric with said axis and having a transverse second end face adjacent said first end face, a turbine housing at one end of said second hollow casing and effective to discharge turbine exhaust air into said second hollow casing, means interengaging said first hollow casing and said second hollow casing for relative rotation about said axis and yieldably against relative separation along said axis, means extending through said barrier plate to the interior of said bell housing and to the interior of said second hollow casing for supplying drive air to said turbine housing, means defining a passageway through said interengaging means for conducting turbine exhaust air from within said second hollow casing to the atmosphere, and means for conducting turbine exhaust air from said second hollow casing through said supporting block and to said passageway.

* * * * *